(12) United States Patent
Aikawa

(10) Patent No.: US 8,480,232 B2
(45) Date of Patent: Jul. 9, 2013

(54) OPHTHALMOLOGIC APPARATUS

(75) Inventor: Satoshi Aikawa, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/208,377

(22) Filed: Aug. 12, 2011

(65) Prior Publication Data

US 2012/0050672 A1 Mar. 1, 2012

(30) Foreign Application Priority Data

Aug. 30, 2010 (JP) ................................. 2010-192707

(51) Int. Cl.
  *A61B 3/14* (2006.01)
  *A61B 3/00* (2006.01)

(52) U.S. Cl.
  USPC ............ 351/206; 351/246; 351/208; 351/210

(58) Field of Classification Search
  USPC .................................................. 351/200–246
  See application file for complete search history.

(56) References Cited

U.S. PATENT DOCUMENTS

| 7,677,730 B2 | 3/2010 | Shimizu |
| 7,918,557 B2 | 4/2011 | Iwanaga et al. |
| 7,926,945 B2 * | 4/2011 | Dick et al. .................... 351/206 |
| 8,070,291 B2 | 12/2011 | Iwanaga et al. |
| 2008/0018854 A1* | 1/2008 | Matsumoto .................... 351/206 |
| 2008/0212027 A1 | 9/2008 | Shimizu |
| 2010/0123871 A1 | 5/2010 | Iwanaga et al. |
| 2010/0123872 A1 | 5/2010 | Aikawa et al. |
| 2010/0238402 A1* | 9/2010 | Itoh et al. ....................... 351/206 |
| 2011/0149243 A1 | 6/2011 | Iwanaga et al. |

FOREIGN PATENT DOCUMENTS

| JP | 07-008459 A | 1/1995 |
| JP | 2003-305009 A | 10/2003 |
| JP | 2008-212327 A | 9/2008 |
| JP | 2008-212375 A | 9/2008 |

OTHER PUBLICATIONS

Communication dated Dec. 15, 2011, forwarding a European Search Report dated Dec. 5, 2011, in European Application No. 11177043.4-1265.

* cited by examiner

*Primary Examiner* — Mohammed Hasan
(74) *Attorney, Agent, or Firm* — Fitzpatrick, Cella, Harper & Scinto

(57) ABSTRACT

A fundus imaging apparatus comprises: a plurality of light source modules with different wavelengths; a moving unit adapted to move one of the plurality of light source modules to a position to illuminate a fundus of an eye to be examined through an illumination optical system, based on a selected imaging mode; and an image sensor which captures feedback light from the fundus of the eye illuminated through the illumination optical system.

21 Claims, 4 Drawing Sheets

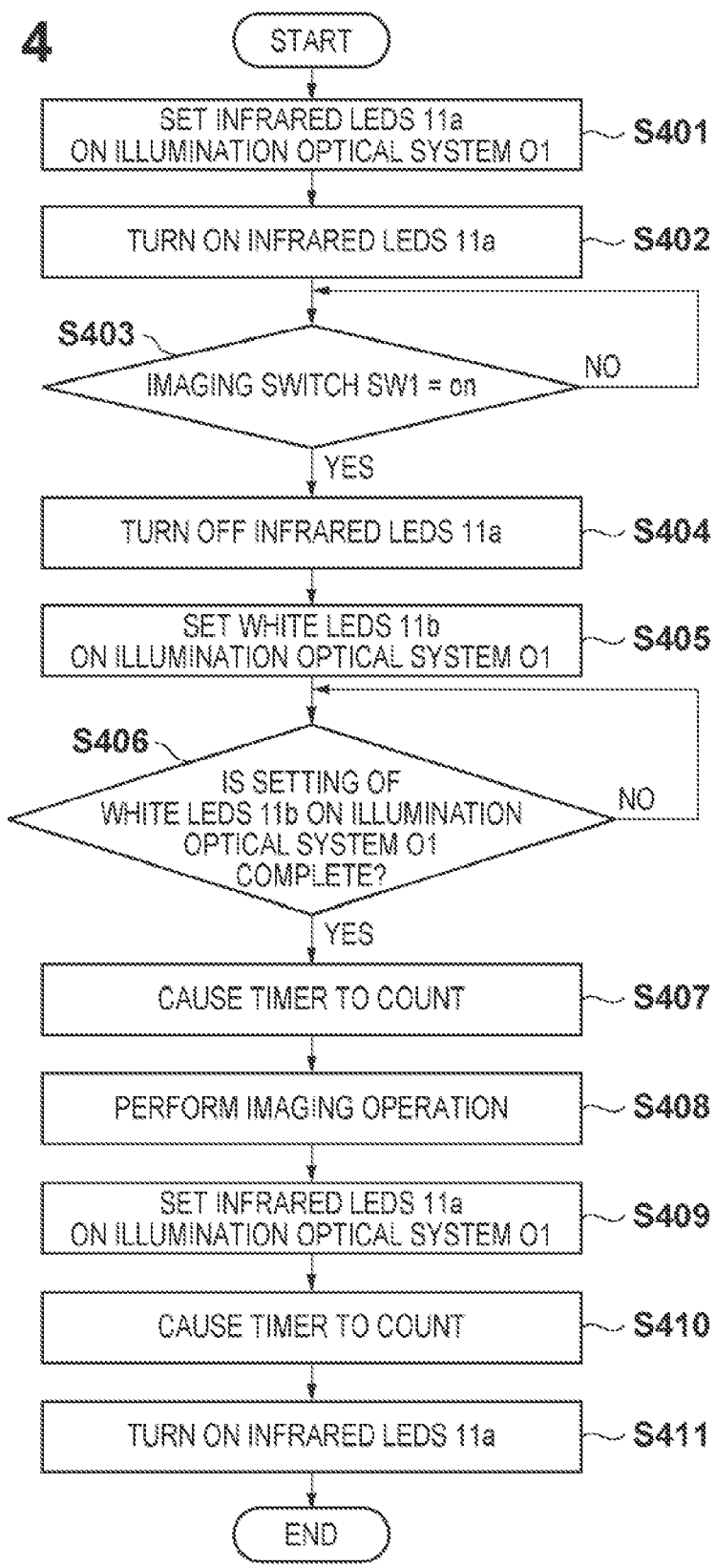

OPHTHALMOLOGIC APPARATUS

BACKGROUND OF THE INVENTION

1. Field of the Invention

The present invention relates to a fundus imaging apparatus and, more particularly, to a fundus imaging apparatus which uses infrared light as an observation light source and white light as an imaging light source.

2. Description of the Related Art

A fundus imaging apparatus, in particular a non-mydriatic fundus camera, generally uses infrared light as an observation light source to prevent the constriction of the pupils for an object being examined, and visible light as an imaging light source to obtain a color image.

As an infrared light source, an infrared light component extracted from light from a white halogen lamp through an optical filter has been used. Advances in LED technology, however, have recently begun to allow the single use of an infrared LED. As a visible light source, an Xe tube is still used to instantaneously obtain a sufficient amount of light.

Recently, even a white LED which emits a sufficient amount of light has been developed. This has increased the possibility of implementing a visible light source using a white LED.

Japanese Patent Laid-Open No. 07-008459 discloses a technique for mechanically switching between infrared light and visible light by switching an optical filter to be placed in front of a light source for emitting light with a broad wavelength between an infrared transmission filter and a visible light transmission filter.

Japanese Patent Laid-Open No. 2008-212327 discloses a technique for obtaining an annular surface light source by alternately arranging infrared LEDs and white LEDs in an annular form. Infrared light and visible light are electrically switched.

Japanese Patent Laid-Open No. 2008-212375 discloses a technique for eliminating light source irregularity by rotating LED light sources discontinuously arranged in an annular form at the time of imaging.

In general, an observation light source and an imaging light source are selectively used by electrical switching, with an optical path being divided by a dichroic mirror. However, the intervention of the dichroic mirror causes a light amount loss. In addition, dividing the optical path requires to prepare optical paths at two portions, resulting in an increase in space for the optical paths. This leads to increases in apparatus size and the complexity of the structure and components.

According to Japanese Patent Laid-Open No. 07-008459, a compact light source called an LED light source does not exhibit a broadband characteristic as a light emission characteristic, and hence cannot be a light source which covers light ranging from infrared light to visible light. In addition, this device needs to prepare two optical filters in addition to a light source. That is, the device includes many constituent elements and has a complicated arrangement.

According to Japanese Patent Laid-Open No. 2008-212327, since infrared LEDs and white LEDs are alternately arranged on one circumference, the pitches between the infrared LEDs and between the white LEDs are large. For this reason, this light source cannot be a satisfactory light source as an observation/imaging light source required to provide uniform illumination in an annular form.

The light source disclosed in Japanese Patent Laid-Open No. 2008-212375 may possibly be put to practical use as an observation light source owing to an afterimage phenomenon. When, however, using this light source as an imaging light source, it is necessary to prolong the exposure time. This leads to image blur due to fixation disparity. It is therefore impossible to obtain a captured image with sufficient quality.

In consideration of the above problem, the present invention provides a technique of switching a plurality of light sources with a compact, simple arrangement while reducing a light amount loss.

SUMMARY OF THE INVENTION

According to one aspect of the present invention, there is provided a fundus imaging apparatus comprising: a plurality of light source modules with different wavelengths; a moving unit adapted to move one of the plurality of light source modules to a position to illuminate a fundus of an eye to be examined through an illumination optical system, based on a selected imaging mode; and an image sensor which captures feedback light from the fundus of the eye illuminated through the illumination optical system.

According to one aspect of the present invention, there is provided a fundus imaging apparatus comprising: an infrared light source provided on an illumination optical system which illuminates an eye to be examined; a white light source provided on the illumination optical system; and a control unit adapted to perform control to retract the infrared light source from an optical path of the illumination optical system and insert the white light source onto the optical path, when imaging the eye.

Further features of the present invention will be apparent from the following description of exemplary embodiments with reference to the attached drawings.

BRIEF DESCRIPTION OF THE DRAWINGS

FIG. 4 is a flowchart showing a processing procedure in the light source unit.

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

(First Embodiment)

Figure 1:
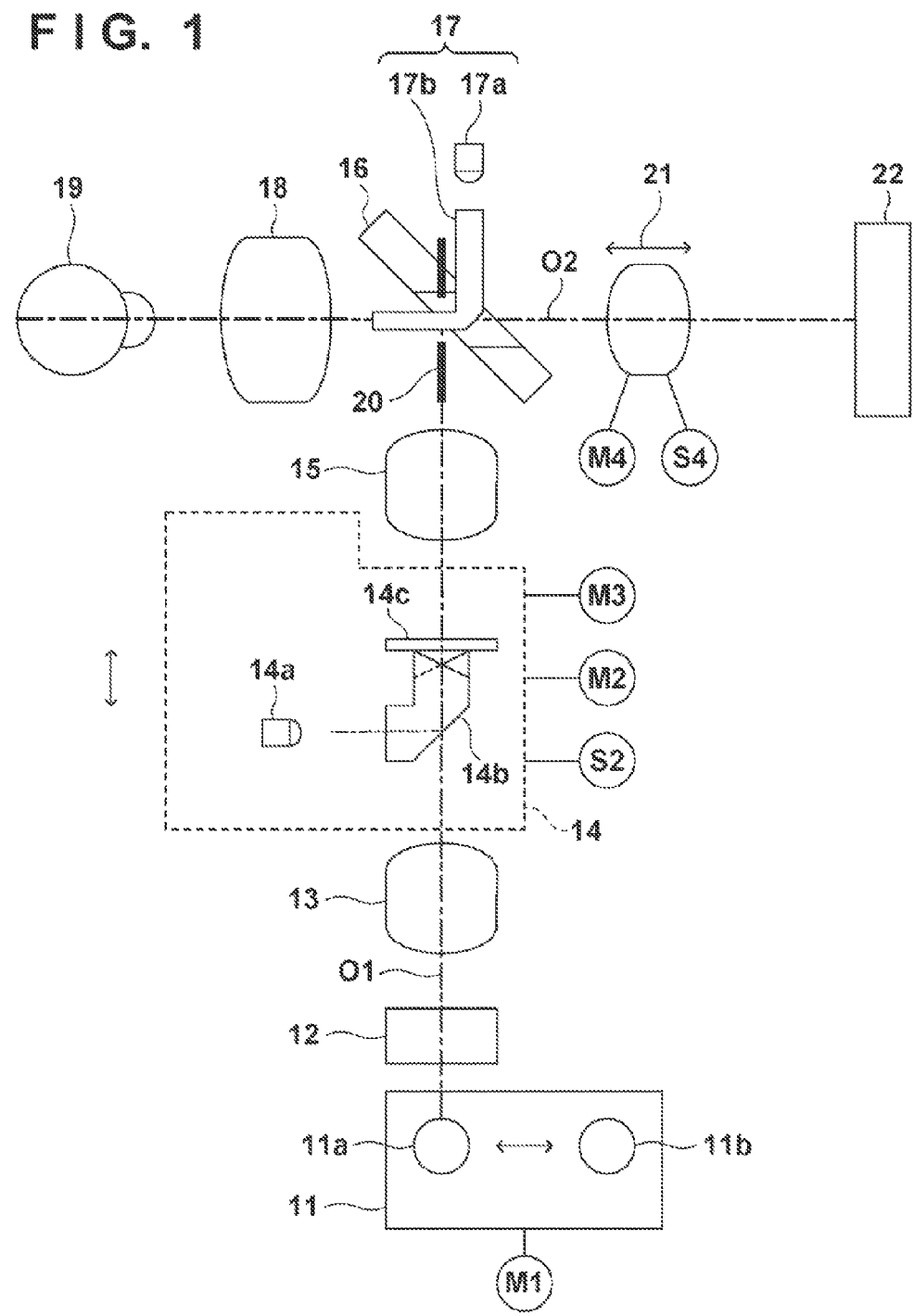
FIG. 1 is a view showing the schematic arrangement of a fundus imaging apparatus.

The schematic arrangement of a fundus imaging apparatus will be described below with reference to FIG. 1. This fundus imaging apparatus is roughly constituted by an illumination optical system O1 and an observation/imaging optical system O2. A light source unit 11 includes infrared LEDs 11a as infrared light sources and white LEDs 11b as visible light sources (white light sources). A light source driving motor M1 switches the LEDs to face the illumination optical system O1 between the infrared LEDs 11a and the white LEDs 11b. A ring slit 12 is a mask member which is perpendicular to the illumination optical system O1 to form an annular mask and adjusts illumination light from the light source unit 11 into ring-like illumination light. An illumination lens 13 and an illumination relay lens 15 focus ring illumination on an eye 19 that is to be examined. A split unit 14 includes a focus index light source 14a for projecting a focus index, a prism 14b for splitting a light source, and a focus index mask 14c for indicating the outer shape of the focus index. The split unit 14 moves (inserts) the prism 14b and the focus index mask 14c onto the optical path of the illumination optical system O1 at the time of observation. The split unit 14 further includes a moving mechanism which moves in the directions indicated by the arrows in FIG. 2 to shift/move the focus index in the optical axis direction and a retraction mechanism for retracting the focus index from the optical path of the illumination optical system O1.

A split shift driving motor M2 shifts/drives the split unit 14 to focus on the focus index. A split position detection sensor S2 detects the stop position of the split unit 14. A split moving driving motor M3 moves the split unit 14 backward and forward relative to the illumination optical system O1. That is, at the time of observation, the split moving driving motor M3 is controlled to move (insert) the split unit 14 into the illumination optical system O1 to project the split index in an observation image. At the time of imaging, the split moving driving motor M3 is controlled to retract the split unit 14 from the illumination optical system O1 so as to prevent the focus index from being depicted in a captured image. A perforated mirror 16 is a total reflection mirror having a hole in the center, which is configured to reflect ring-like illumination light by its mirror portion on the outer periphery and transmit imaging light through the hole in the center. An alignment index projection unit 17 includes a light source 17a for projecting an alignment index and a light guide 17b which forms an index.

An objective lens 18 focuses the ring illumination reflected by the perforated mirror 16 onto the eye 19 to illuminate the fundus of the eye in a ring-like form. The objective lens 18 focuses the fundus image of the illuminated eye onto the position of a stop 20 near the perforated mirror. The light further propagates in the observation/imaging optical system O2. A focus lens 21 is a lens for adjusting the focus of an imaging light beam passing through the hole in the center of the perforated mirror 16. The focus lens 21 moves in the directions indicated by the arrows in FIG. 1 to perform focus adjustment. A focus lens driving motor M4 drives the focus lens 21 to adjust its focus. A focus lens position detection unit S4 detects the stop position of the focus lens 21. An imaging element 22 forming an image sensor photoelectrically converts imaging light. A processing circuit (not shown) A/D-converts the electrical signal obtained by the imaging element 22. A display device (not shown) then displays the signal at the time of observation with infrared light. This signal is stored in a recording medium at the time of imaging.

Figure 2:
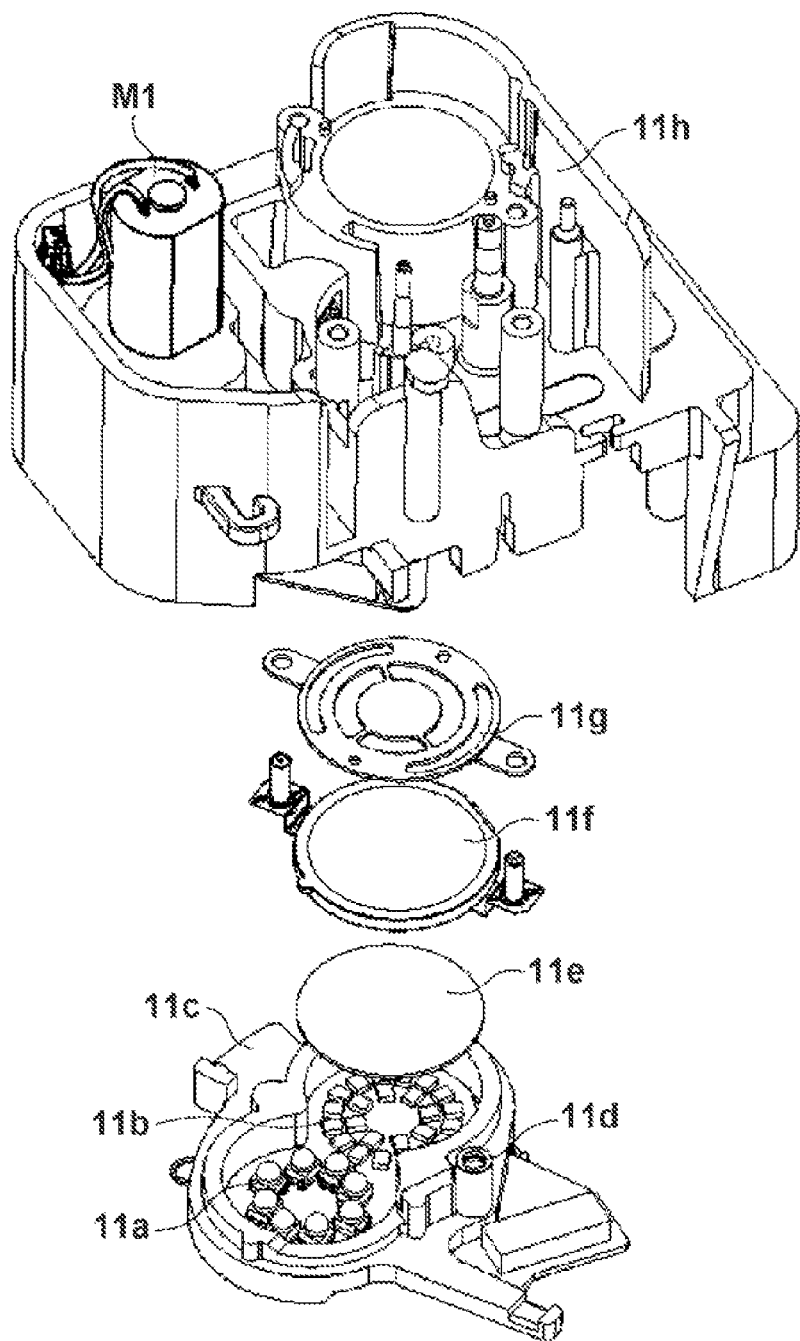
FIG. 2 is a development view of a light source unit.

The light source unit 11 will be described in detail below with reference to FIG. 2. The light source unit 11 includes the infrared LEDs 11a, the white LEDs 11b, an LED holder 11c, an LED holder hole 11d, a diffusion sheet 11e, a condenser lens 11f, ring slits 11g, a light source ground plate 11h, and the light source driving motor M1.

Both the infrared LEDs 11a and the white LEDs 11b are obtained by arranging LEDs placed in surface mount type packages on a single printed circuit board in an annular form, and integrally mounting them on the LED holder 11c. With this arrangement, light from the light source unit 11 roughly becomes annular light. The LED holder hole 11d is formed in the LED holder 11c. The LED holder hole 11d is parallel to the illumination optical system O1, and is fitted on a shaft (not shown) formed on the light source ground plate 11h and rotatably fixed. The diffusion sheet 11e and the condenser lens 11f diffuse light beams from the infrared LEDs 11a and the white LEDs 11b to eliminate illumination irregularity caused by the LEDs, thereby obtaining uniform illuminance.

The ring slits 11g are mask members for masking unnecessary portions of a light beam, which is uniformized into a roughly annular shape, to form it into an accurate annular shape.

That is, the infrared LEDs 11a or the whites LED 11b of the light source unit 11 are arranged such that the annular array of them faces the annular aperture of the ring slit 12 when facing the illumination optical system O1. These elements are mounted on the light source ground plate 11h. These constituent elements are fixed on the light source ground plate 11h, together with the light source driving motor M1. When power is supplied to the light source driving motor M1, the LED holder 11c rotates relative to the light source ground plate 11h. The LED holder 11c is then positioned by a stopper (not shown). When the LED holder 11c is in the state shown in FIG. 2, the white LEDs 11b face the illumination optical system O1. When the LED holder 11c rotates, the infrared LEDs 11a face the illumination optical system O1.

Figure 3:
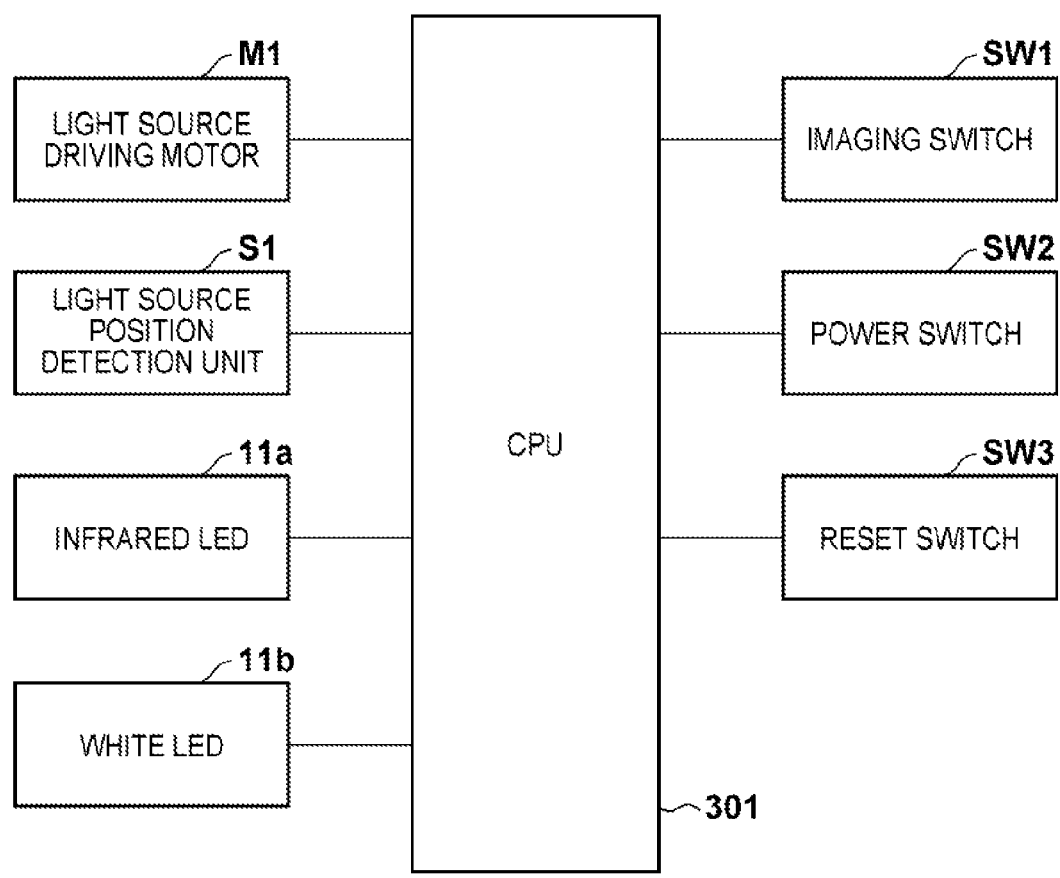
FIG. 3 is a view showing the functional arrangement of the light source unit.

That is, the light source driving motor M1 to be described later with reference to FIG. 3 can move one of a plurality of light source modules including the infrared LEDs 11a (first light source modules) and the white LEDs 11b (second light source modules), within a plane perpendicular to an optical path along which ring-like illumination light is guided, to a position where the center of the light source module coincides with the center axis of the optical path. The light source driving motor M1 can also move one of the plurality of light source modules to a position where the center of the light source module does not coincide with the center axis of the optical path. It is possible to move one of the plurality of light source modules to positions where the center of the light source module coincides and does not coincide with the center axis of the optical path within the same plane. These elements may be mounted on a single printed circuit board. Note that it is also possible to move one of the plurality of light source modules, by rotational movement with reference to an axis parallel to the center axis of the optical path, from a position where the center of the light source module does not coincide with the center axis of the optical path to a position where they coincide with each other or from a position where the center of the light source module coincides with the center axis of the optical path to a position where they do not coincide with each other.

The functional arrangement of the light source unit will be described with reference to FIG. 3. A CPU 301 controls all the operations in the fundus imaging apparatus. A light source position detection unit S1 detects a light source facing the illumination optical system O1. The light source driving motor M1 can control a desired light source to make it face the illumination optical system O1. It is possible to control the emission intensities of the infrared LEDs 11a and white LEDs 11b as well as turning on/off operation. Upon detecting switching operation with an imaging switch SW1, the apparatus starts imaging operation.

A power switch SW2 turns on or off the power supply of the overall fundus imaging apparatus. After the fundus imaging apparatus is started, the apparatus may be set in a predetermined imaging mode. The predetermined imaging mode is one of imaging modes using infrared LEDs having an emission peak wavelength in the infrared band, white LEDs having an emission peak wavelength in the visible region, LEDs of a specific color having a specific wavelength as an emission peak wavelength, and the like. A reset switch SW3 resets the operation of the CPU 301 at the occurrence of abnormal operation, and restarts the operation. After the reset operation, the apparatus may be set in a predetermined imaging mode.

A processing procedure in the light source unit using the above functional arrangement will be described with reference to the flowchart of FIG. 4. First of all, the processing starts when the power supply is turned on with the power switch SW2.

In step S401, the CPU 301 sets the infrared LEDs 11a so as to make them face the illumination optical system O1. The CPU 301 drives the light source driving motor M1 while monitoring the position of the light sources with the light source position detection unit S1.

In step S402, the CPU 301 continuously turns on the infrared LEDs 11a and keeps them on to observe the fundus. Since the infrared LEDs apply light to the eye 19, the pupils do not constrict. This allows the examiner to perform alignment by using a monochrome image.

In step S403, the CPU 301 checks the state of the imaging switch SW1 and determines whether the imaging switch SW1 is ON. Upon determining that the imaging switch SW1 is ON (YES in step S403), the process advances to step S404. Upon determining that the imaging switch SW1 is not ON (NO in step S403), the CPU 301 waits until the imaging switch SW1 is turned on.

In step S404, the CPU 301 turns off the infrared LEDs 11a. Owing to an attempt to move the light source unit 11, the CPU 301 turns off the illumination light sources which are ON because the illumination irregularity increases during operation.

In step S405, the CPU 301 starts the operation of setting the white LEDs 11b on the illumination optical system O1.

In step S406, the light source driving motor M1 moves the white LEDs 11b necessary for imaging operation while monitoring the position of the light sources with the light source position detection unit S1. The CPU 301 then determines whether the operation of setting the white LEDs 11b on the illumination optical system O1 is complete. If the CPU 301 determines that the operation is complete (YES in step S406), the process advances to step S407. If the CPU 301 determines that the operation is not complete (NO in step S406), the CPU 301 waits until the operation is complete.

In step S407, the CPU 301 counts a predetermined time by using a timer. The CPU 301 causes the timer to count in consideration of the time during which the white LEDs 11b bound due to backlash of stopping even when the light source driving motor M1 stops driving.

In step S408, the image sensor shifts to an imaging state and performs imaging operation. More specifically, the digital camera starts exposure, and the CPU 301 turns on the white LEDs 11b. When the white LEDs 11b are turned off, since the exposure finishes, the digital camera finishes the exposure.

In step S409, the CPU 301 sets the infrared LEDs 11a on the illumination optical system O1.

In step S410, like step S407, the CPU 301 causes the timer to count while regarding the time by which the bounding of the infrared LEDs 11a comes to an end as the time during which the infrared LEDs 11a are moving.

In step S411, the CPU 301 turns on the infrared LEDs 11a and shifts to a fundus observation state after the lapse of a predetermined time since the completion of the movement. The CPU 301 turns on/off the light sources depending on whether they are moving. Thereafter, the processing is terminated.

According to the present invention, the simple, compact arrangement can implement switching of the observation light source/imaging light source without light amount loss.

(Second Embodiment)

In observation of a fundus image, it is effective to check a disease by imaging with a specific wavelength. In this case, an optical filter which cuts light beams with wavelengths other than a specific wavelength is generally placed on the imaging light source. An application of the fundus imaging apparatus according to the present invention to such a case will be briefly described below.

The above description is about the imaging light source and the observation light source in the first embodiment, in which the white LEDs are used as the imaging light source. However, it is possible to acquire various kinds of images in accordance with imaging modes by using LEDs of a specific color instead of the white LEDs. In this case, infrared LEDs, white LEDs, and LEDs of a specific color are arranged on an LED holder 11c in an annular form, and LEDs corresponding to a selected mode are made to face an illumination optical system, thereby implement imaging with a specific wavelength. In this case, a plurality of imaging modes with different imaging conditions may be switched by imaging mode switching operation to move one of a plurality of light source modules which corresponds to the imaging mode set by switching within a plane perpendicular to the optical path so as to make the center of the light source module coincide with the center axis of the optical path. The imaging mode switching operation is executed by the CPU 301.

Using this arrangement can implement a fundus imaging apparatus which can perform imaging with a specific wavelength, with a simple, compact arrangement, without light amount loss.

According to the present invention, it is possible to switch a plurality of light sources with a compact, simple arrangement while reducing a light amount loss.

(Other Embodiments)

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-192707 filed on Aug. 30, 2010, which is hereby incorporated by reference herein in its entirety.

What is claimed is:

1. An ophthalmologic apparatus comprising:
a plurality of light sources with different wavelengths;
a moving unit adapted to move one of said plurality of light sources to a position to illuminate a fundus of an eye to be examined through an illumination optical system, based on a selected imaging mode;
an image sensor which captures feedback light from the fundus of the eye illuminated through the illumination optical system; and
a turning on/off unit adapted to turn off said light source while said light source is moved by said moving unit, and to turn on said light source after the lapse of a predetermined time since completion of movement.

2. The apparatus according to claim 1, further comprising:
an adjustment unit adapted to adjust a light beam from a light source of said plurality of light sources into ring-like illumination light; and
a light guide unit adapted to guide the ring-like illumination light to the fundus of the eye.

3. The apparatus according to claim 2, wherein said moving unit moves one of said plurality of light sources, within a plane perpendicular to an optical path of the ring-like illumination light guided by said light guide unit, to a position where a center of said light source coincides with a center axis of the optical path.

4. The apparatus according to claim 3, wherein said moving unit is configured to further move said one light source from a position where the center of said light source coincides with the center axis of the optical path to a position where the center of said light source does not coincide with the center axis of the optical path.

5. The apparatus according to claim 4, wherein said plurality of light sources include (a) a first light source having an emission peak wavelength in an infrared band and (b) a second light source having an emission peak wavelength in a visible region.

6. The apparatus according to claim 5, wherein said image sensor is used to observe or capture a fundus image of the eye,
wherein an observation mode of observing a fundus image with said image sensor is switched to an imaging mode of capturing a fundus image, when said moving unit switches a light source to be set from said first light source to said second light source, and
wherein the imaging mode is switched to the observation mode, when said moving unit switches a light source to be set from said second light source to said first light source.

7. The apparatus according to claim 3, wherein said moving unit is configured to move one of said plurality of light sources, by rotational movement with reference to an axis parallel to the center axis of the optical path, from a position where the center of said light source does not coincide with the center axis of the optical path to a position where the center of said light source coincides with the center axis of the optical path.

8. The apparatus according to claim 2, wherein a light source of said plurality of light sources comprises an LED.

9. The apparatus according to claim 8, wherein said adjustment unit comprises a mask member having an annular aperture for adjusting a light beam from said light source into ring-like illumination light, and
wherein said light source includes a plurality of LEDs arranged in an annular form so as to face the annular aperture of said mask member.

10. The apparatus according to claim 2, wherein said plurality of light sources are arranged within a plane perpendicular to the optical path both when said light source is at a position where the center of said light source coincides the center axis of the optical path and when said light source is at a position where the center of said light source does not coincide the center axis of the optical path.

11. The apparatus according to claim 10, wherein said plurality of light sources are mounted on one printed circuit board.

12. The apparatus according to claim 1, further comprising an imaging mode switching unit adapted to switch a plurality of imaging modes for imaging under different imaging conditions,
wherein said moving unit moves one of said plurality of light sources which corresponds to an imaging mode set by switching by said imaging mode switching unit.

13. The apparatus according to claim 12, wherein said imaging mode switching unit performs switching to a predetermined imaging mode after the apparatus is started or reset, and
wherein said moving unit moves said light source corresponding to the predetermined imaging mode, within a plane perpendicular to the optical path, to a position where the center of said light source coincides with the center axis of the optical path, after the apparatus is started or reset.

14. The apparatus according to claim 1, wherein a first light source of said plurality of light sources is provided at the position, and
wherein said moving unit moves, instead of said first light source provided at the position, a second light source of said plurality of light sources which is different from said first light source to the position.

15. The apparatus according to claim 14, wherein both said first light source and said second light source are provided on a holder, and
wherein said moving unit moves, instead of the first light source, the second light source to the position, by moving the holder.

16. An ophthalmologic apparatus comprising:
an infrared light source provided on an illumination optical system which illuminates an eye to be examined;
a white light source;
a control unit adapted to perform control to retract said infrared light source from an optical path of said illumination optical system and to insert said white light source onto the optical path, when imaging the eye; and
a turning on/off unit adapted to turn off a light source while said light source is moved, and to turn on said light source after the lapse of a predetermined time since completion of movement.

17. The apparatus according to claim 16, wherein said control unit retracts said infrared light source from an optical path of said illumination optical system and inserts said white light source onto the optical path, after controlling said infrared light source which has been turned on to be lowered.

18. The apparatus according to claim 17, wherein said control unit turns on said white light source after said white light source has been inserted onto the optical path.

19. The apparatus according to claim 16, wherein both said infrared light source and said white light source are provided on a holder, and
wherein said control unit retracts said infrared light source from the optical path and inserts said white light source onto the optical path by moving the holder.

20. A method for use with an ophthalmologic apparatus including a plurality of light sources with different wavelengths, the method comprising:
moving one of the plurality of light sources to a position to illuminate a fundus of an eye to be examined through an illumination optical system, based on a selected imaging mode, wherein the apparatus further includes an image sensor which captures feedback light from the fundus of the eye illuminated through the illumination optical system; and
turning off the light source while the light source is moved, and turning on the light source after the lapse of a predetermined time since completion of movement.

21. A method for use with an ophthalmologic apparatus including (a) an infrared light source provided on an illumination optical system which illuminates an eye to be examined, and (b) a white light source, the method comprising:

performing control to retract the infrared light source from an optical path of the illumination optical system and to insert the white light source onto the optical path, when imaging the eye; and turning off a light source while the light source is moved, and turning on the light source after the lapse of a predetermined time since completion of movement.

* * * * *